United States Patent [19]
Caizza et al.

[11] Patent Number: 5,487,733
[45] Date of Patent: Jan. 30, 1996

[54] ASSEMBLY WITH COLLAPSIBLE SHEATH AND TIP GUARD

[75] Inventors: Richard J. Caizza, Barry Lakes; Jon S. Bell, Midland Park, both of N.J.

[73] Assignee: Becton, Dickinson and Company, Franklin Lakes, N.J.

[21] Appl. No.: 420,890

[22] Filed: Apr. 11, 1995

Related U.S. Application Data

[63] Continuation of Ser. No. 309,372, Sep. 20, 1994, abandoned.

[51] Int. Cl.$^6$ .................................................. A61M 5/00
[52] U.S. Cl. ......................... 604/110; 604/198; 604/263
[58] Field of Search .................................. 604/110, 187, 604/192, 198, 263

[56] References Cited

U.S. PATENT DOCUMENTS

| | | | |
|---|---|---|---|
| 4,139,009 | 2/1979 | Alvarez | 128/218 |
| 4,998,922 | 3/1991 | Kuracina et al. | 604/192 |
| 5,304,151 | 4/1994 | Kuracina | 604/198 |
| 5,328,482 | 7/1994 | Sircom et al. | 604/198 X |
| 5,334,149 | 8/1994 | Nortman et al. | 604/110 |

*Primary Examiner*—John D. Yasko
*Attorney, Agent, or Firm*—Vincent A. Castiglione

[57] ABSTRACT

A needle cannula is surrounded by a collapsible sheath and a spring that is expandable and retractable independent of the sheath. A tip guard is mounted to either the distal end of the sheath or the distal end of the spring. The tip guard is movable to protectively cover the tip of the needle cannula as the spring expands independently of the sheath. Proximally directed forces on the tip guard will merely urge the tip guard into tighter protective engagement with the distal tip of the needle cannula without exposing the needle cannula. However, the needle cannula can intentionally be re-exposed by merely collapsing the spring in a proximal direction.

28 Claims, 6 Drawing Sheets

ASSEMBLY WITH COLLAPSIBLE SHEATH AND TIP GUARD

This application is a continuation of application Ser. No. 08/309,372, filed Sep. 20, 1994 now abandoned.

BACKGROUND OF THE INVENTION

1. Field of the Invention

The subject invention relates to needles with collapsible sheaths and tip guards to prevent accidental needle sticks.

2. Description of the Prior Art

A needle cannula includes opposed proximal and distal ends and a lumen extending therebetween. Normally, the proximal end of the prior art needle cannular is mounted to a hub for placing the lumen in communication with a medical instrument, such as a hypodermic syringe, while the distal end of the prior art needle cannula is typically beveled to define a sharply pointed tip. Health care workers and patients can be stuck accidentally with the distal tip of a needle cannula. An accidental stick occurring prior to use of the needle cannula is painful and can cause infection. An accidental stick occurring after use of a needle cannula can further transmit disease.

Most prior art needle cannulas are provided with shields that are intended to reduce the risk of accidental sticks. Some prior art shields include a resiliently collapsible sheath that surrounds the needle cannula prior to use. In use, these sheaths extend distally beyond the needle cannula, and consequently will contact the skin of the patient prior to making an injection. The sheaths expand radially and collapse axially as the needle cannula is moved toward and into the patient. The sheath then resiliently returns to an axially extended, radially contracted condition as the needle cannula is withdrawn from the patient. An example of a prior art collapsible sheath for a needle cannula is shown in U.S. Pat. No. 4,139,009. Prior art needle cannulas with collapsible sheaths present a false sense of security. Health care workers may assume that the covered needle is safely protected. However, any proximally directed force on the distal end of the sheath will expose the needle cannula and create the potential for accidental needle sticks.

More recent prior art includes a collapsible sheath that is closely surrounded by a coil spring. The proximal end of the coil spring is fixed near the proximal end of the sheath. However, remaining portions of the coil spring can be collapsed in a proximal direction independent of the sheath. The sheath functions substantially as in the above described U.S. Pat. No. 4,139,009 when the coil spring is collapsed. However, the coil spring can be released to expand axially and closely surround the sheath. The coil spring is intended to prevent the radial expansion of the sheath that is required to axially collapse the sheath. Hence, the coil spring is intended to keep the sheath in its extended position. This combination of a sheath closely surrounded by a coil spring is shown in U.S. Pat. No. 4,998,922.

The above described combination of a collapsible sheath closely surrounded by an independently collapsible coil spring is still not a completely satisfactory approach to the aforementioned concerns. For example, the sheath may not completely return to its fully extended position. The coil spring, therefore, will not have a free path of travel into its fully extended condition. Ideally, the expanding coil spring will generate the full extension of the sheath. However, the close engagement between the sheath and the coil spring can cause the coil spring to bind prior to reaching its fully extended condition, and therefore will leave the distal tip of the needle exposed. Even when the sheath and the coil spring are fully extended and cover the distal tip of the needle, proximally directed forces on the sheath can cause sufficient deformation of the sheath, the coil spring and/or the needle cannula to re-expose the distal tip of the used needle cannula. Additionally, the requirement of disposing the coil spring axially around the sheath may be considered aesthetically or functionally undesirable for some applications. Finally, the known combination of a collapsible sheath closely surrounded by a coil spring provides no convenient way to intentionally re-expose the needle cannula. For instance, an intentional re-exposure is desirable in situations where a drug, such as an anesthetic, is administered in small doses over a period of time in accordance with the needs of the patient. Any attempt to intentionally re-expose the needle cannula shown in U.S. Pat. No. 4,998,922 could generate the inadvertent needle stick that the sheath and coil spring are intended to avoid.

Accordingly, there is a need for a device which provides safe, reliable re-exposure of a needle cannula during use while alleviating the risk of accidental needlesticks associated with conventional needle shields, and reducing the problems associated with prior attempts.

SUMMARY OF THE INVENTION

In order to address these and other concerns, a needle assembly for secure, safe re-exposure of a needle cannula is provided. The needle cannula includes opposed proximal and distal ends. Normally, the distal end of the needle cannula is beveled to define a sharp point, while the proximal end of the needle cannula may be mounted to a hub that is selectively engageable with a medical instrument such as a hypodermic syringe, a blood collection tube, or various other medical instruments as known to those skilled in the art. The needle assembly includes a sheath surrounding the needle cannula. The sheath has a proximal end mounted to the needle hub and an opposed distal end. The sheath may alternately be urged from a collapsed condition, where the distal point of the needle cannula is exposed, to an extended condition, where the distal end of the sheath protectively surrounds the distal point of the needle cannula.

The assembly further includes a spring which extends parallel to the sheath. The spring has a proximal end mounted near the proximal end of the sheath and an opposed distal end. The distal end of the spring extends toward the distal point of the needle cannula when the spring is extended toward an unbiased condition. However, the entire spring can be collapsed proximally such that the distal end of the spring is disposed near the hub of the needle cannula.

A tip guard is movably mounted on either the distal end of the spring or the distal end of the sheath, and is urged over the distal tip of the needle cannula in response to the axial extension of the spring. The distal ends of the spring and/or the sheath may define cooperating cam surfaces for moving the tip guard into a position for protectively covering the distal tip of the needle cannula in response to expansion of the spring. A leaf spring :nay be provided to bias the tip guard both toward and in its closed position.

The spring need not circumferentially grip the sheath to prevent the sheath's radial expansion as described in the above-mentioned prior art. Thus, the radial dimensions of the spring are not critical, and the spring can be disposed within the sheath.

BRIEF DESCRIPTION OF THE DRAWINGS

The invention will now be explained in detail by way of reference to the following drawings, wherein;

FIGS. 1a and 1b depict alternate configurations in lieu of the coil spring associated with the subject invention.

FIG. 2 is a side elevational view of the needle assembly of FIG. 1 illustrated in its assembled condition.

FIG. 3 is an end elevational view as viewed from the left side of FIG. 2.

FIG. 4 is a cross-sectional view taken along line 4—4 in FIG. 3.

DETAILED DESCRIPTION OF THE PREFERRED EMBODIMENT

Figure 1:
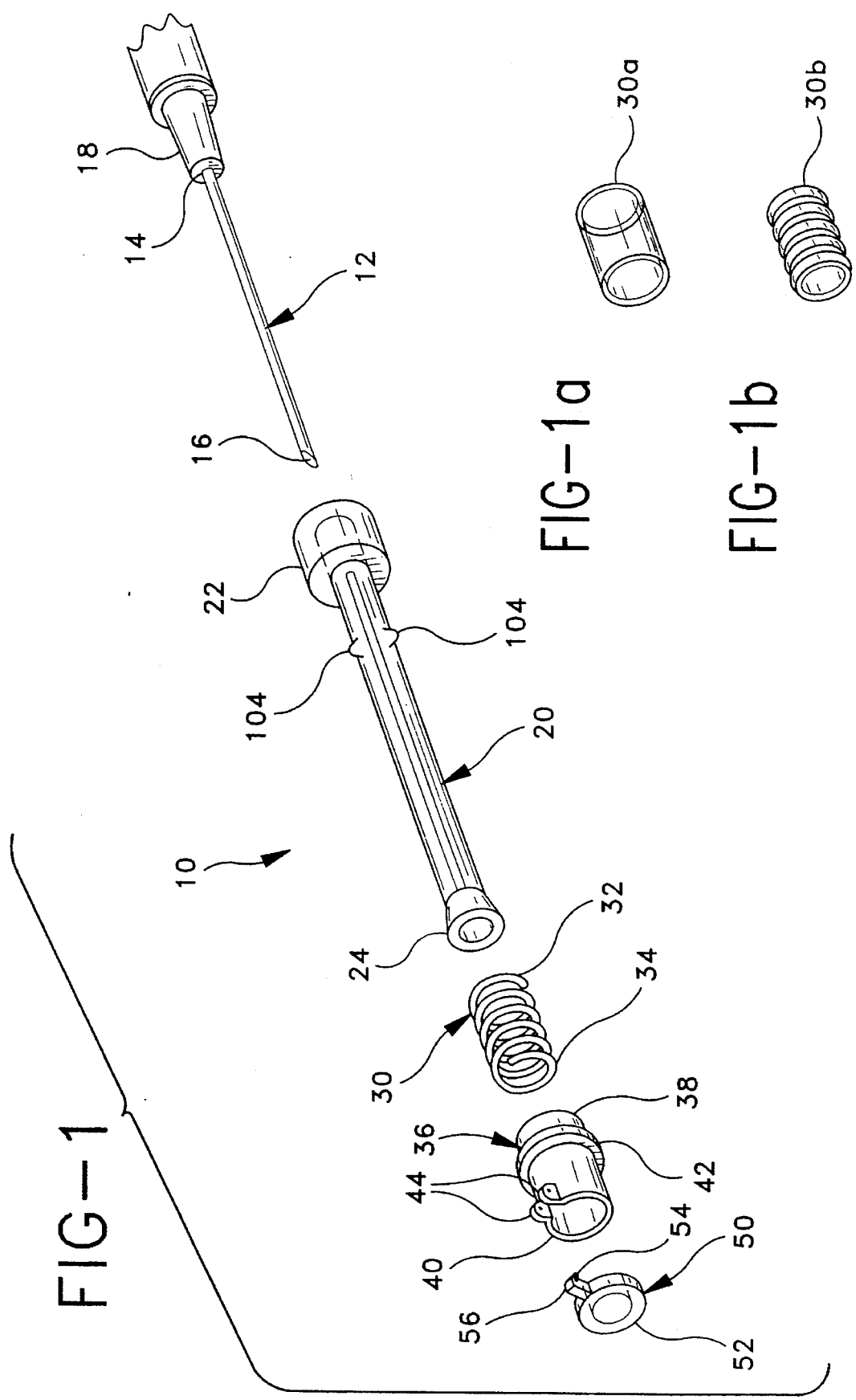
FIG. 1 is an exploded perspective view of a needle assembly with a collapsible sheath and tip guard in accordance with the subject invention.

Turning now to the drawings, wherein like numerals denote like components, a needle assembly in accordance with subject invention is identified generally by the numeral 10 in FIGS. 1–6. Needle assembly 10 includes a needle cannula 12 having a proximal end 14 and an opposed sharply pointed distal end 6. Proximal end 14 of needle cannula 12 may be securely mounted in a needle hub 18 for threaded interconnection with a a medical instrument, such as the luer B collar of a hypodermic syringe. Alternately, as will be appreciated by those skilled in the art, the needle cannula 12 may be of the type utilized for blood collection purposes and, as such, the proximal end 14 and/or needle hub 18 may be appropriately configured for attachment to a blood collection tube or similar vessel. Other types of needle cannulae may be readily afforded with the benefits and advantages of the present invention.

Needle assembly 10 further includes a sheath 20 with opposed proximal and distal ends 22 and 24. Proximal end 22 of sheath 20 defines a hub which is securely mounted to hub 18 of needle cannula 12. Distal end 24 of sheath 20 defines a relatively short, continuous outwardly flared frustum. Portions of collapsible sheath 20 intermediate proximal and distal ends 22 and 24 are resiliently collapsible in response to proximally directed forces on distal end 24. These forces may be generated, for example, by urging the entire needle assembly 10 toward an injection site or withdrawal or collection site, such as a patient or a medical vial, for purposes of administering an injection, or withdrawing or collecting bodily fluid, medication, or the like.

Needle assembly 10 further includes a coil spring 30 having opposed proximal and distal ends 32 and 34, respectively. Proximal end 32 of spring 30 is secured substantially adjacent hub 22 of sheath 20. In the embodiment depicted in FIGS. 1–6, spring 30 surrounds sheath. However, unlike prior art needles discussed above, spring 30 may define a diameter which is substantially greater than the diameter of sheath 20 in the axially extended condition of the sheath depicted in FIGS. 2 and 4. The loose fit reflects the fact that spring 30 performs a different function than springs in the prior art, and ensures that spring 30 will not bind against sheath 20 prior to full extension.

It will be realized by those skilled in the art that other configurations may be utilized in place of the coil spring 30 to achieve the functions herein described. For instance, coil spring 30 may be replaced by an elastomeric collar 30a or an elastomeric resilient bellows 30b as depicted in FIGS. 1a and 1b, respectively. Other configurations will be readily devised by the skilled artisan.

Figures 2, 3, 4:
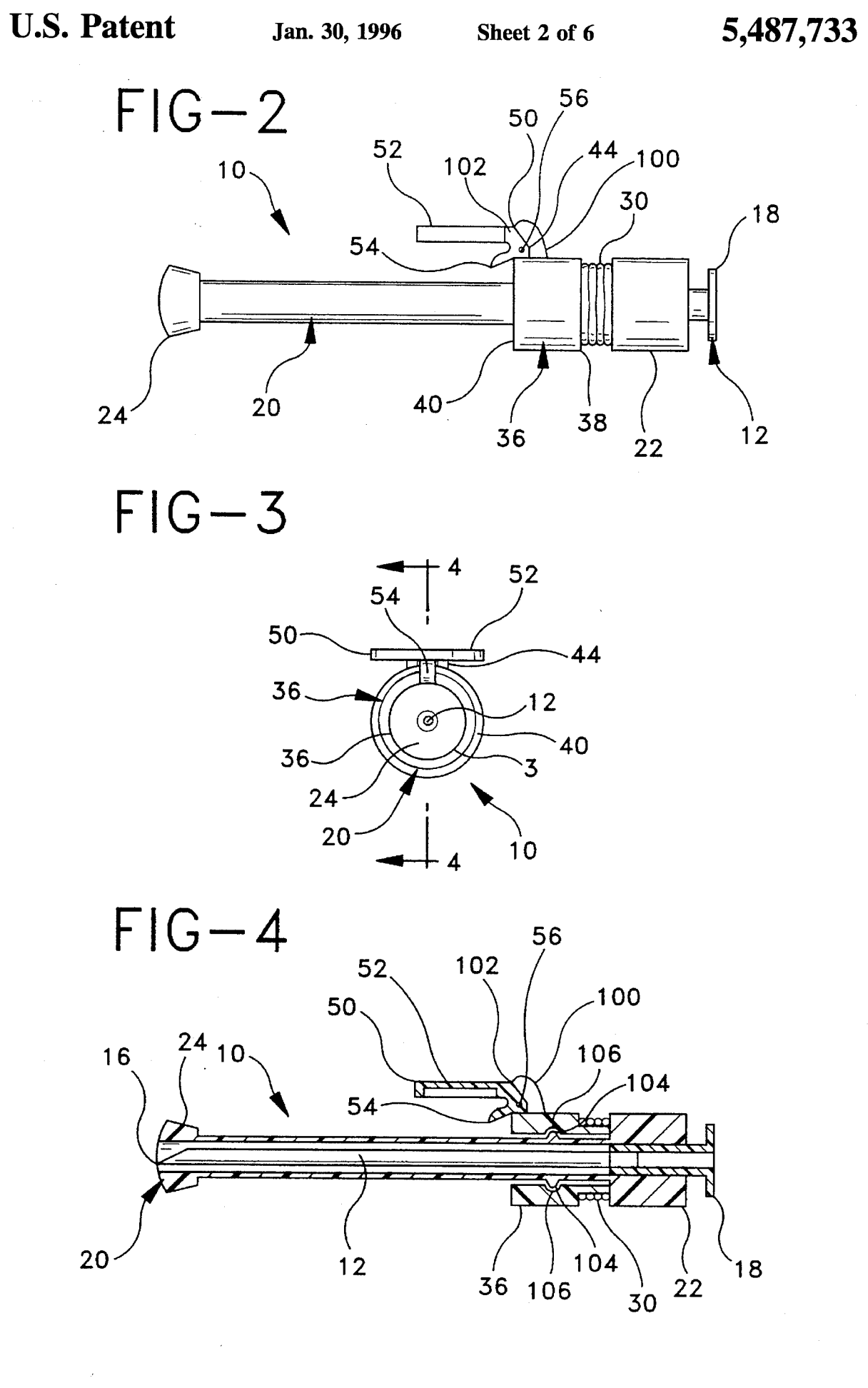
Figure 5:
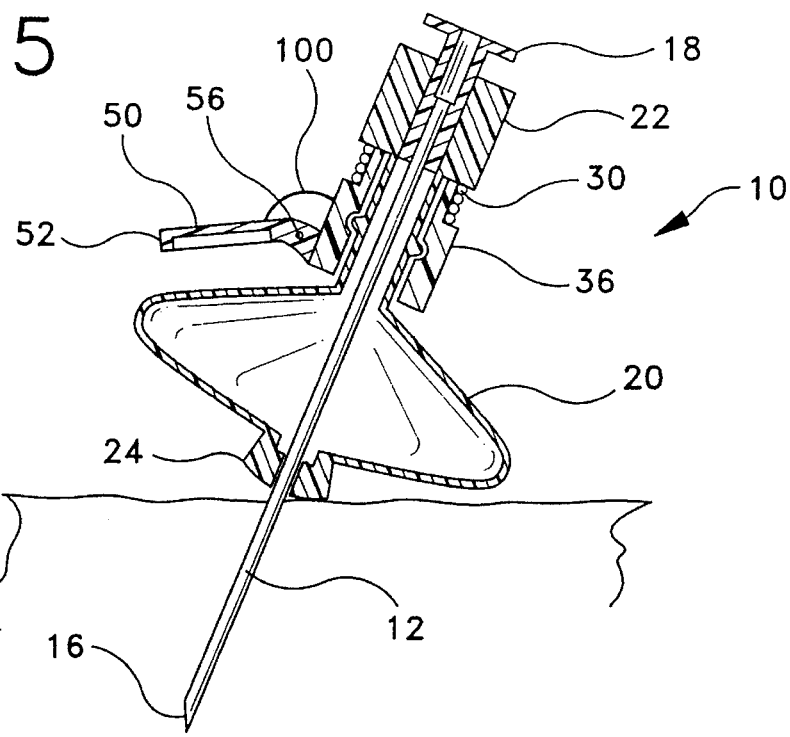
FIG. 5 is a cross-sectional view similar to FIG. 4, but showing the needle assembly during use.

Needle assembly 10 further includes a generally tubular spring collar 36 mounted to distal end 34 of spring 30 and surrounding sheath 20 for slidable movement therealong. Collar 36 includes opposed proximal and distal ends 38 and 40 and an outwardly extending actuator flange 42 therebetween for manually moving collar 36 and spring 30. Collar 36 is configured or otherwise dimensioned to releasably engage portions of sheath 20 on or adjacent hub 22 for selectively retaining spring 30 in a collapsed condition as shown in FIGS. 4 and 5. For instance, sheath 20 may include one or more integrally formed barbs 104 which engage with recesses or other formations 106 configured on collar 36. See FIGS. 1 and 4. The barbs may be configured with a deformable structure and/or may include ramped proximal and/or distal ends to allow collar 36 to be releasably engageable with the sheath 20. Distal end 40 of collar 36 also includes hinge mounts 44 which define a hinge axis of rotation substantially orthogonal to needle cannula 12.

Figure 6:
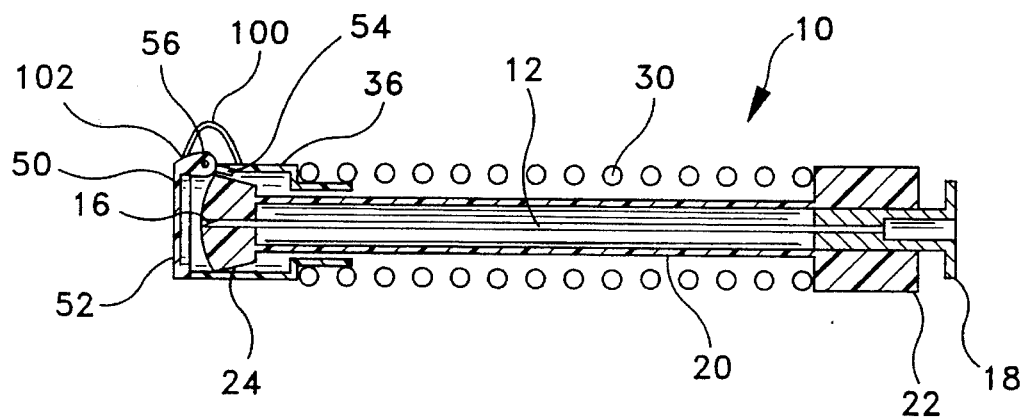
FIG. 6 is a cross-sectional view similar to FIGS. 4 and 5, but showing the needle tip in a fully shielded condition.

Needle assembly 10 further includes a cap 50 having a tip guard 52, an actuator tab 54 and a pivot axis 56 therebetween. Pivot axis 56 is mounted to hinge mounts 44 to permit pivoting of cap 50 relative to collar 36. In a first range of rotational positions of cap 50, as shown in FIGS. 2–5, distal end 40 of collar 36 is open. However, when spring 30 is extended, as shown in FIG. 6, cap 50 is rotated such that tip guard 52 covers distal end 40 of collar 36 and encloses distal tip 16 of needle cannula 12. As shown, a leaf spring 100 may be disposed between the collar 36 and an arm portion 102 of the cap 50 to bias the cap 50 and to assist the cap to rotate between its open position illustrated in FIGS. 2 and 4 and the closed position illustrated in FIG. 6. The biasing action of the leaf spring 100 will further serve to assist the cap to maintain its closed position, once engaged.

The actuator tab 54 of cap 50 is dimensioned to engage the tapered surface of frustum shaped distal end 24 of sheath 20 as spring 30 approaches the fully extended position shown in FIG. 6. This engagement will cause cap 50 to pivot automatically about hinge mounts 44 and into a position where tip guard 52 and collar 36 safely enclose distal tip 16 of needle cannula 12. The biasing action of the spring 100 against arm portion 102 will further assist the pivoting action of the cap 50. Tip guard 52 preferably is formed from a relatively thick rigid thermoplastic material that will exhibit resistance to piercing by distal tip 16 of needle cannula 12. Resistance to piercing can be enhanced by securing a metal safety disk adjacent the proximal surface of tip guard 52.

As shown most clearly in FIGS. 2–4, sheath 20 initially is disposed in an extended position around needle cannula 12 such that distal end 24 of sheath 20 extends distally to or beyond distal tip 16 of needle cannula 12. Collar 36, however, is retained in a proximal position adjacent hub 22 of sheath 20 through its engagement with portions of the sheath 20. This proximal position of collar 36 causes coil spring 30 to be retained in the collapsed condition of FIGS. 2–5. As illustrated in FIG. 5, sheath 20 will collapse in response to a proximally directed force exerted on distal end 24 as needle cannula 12 is urged into an injection site (or collection or withdrawal site), such as a patient, a blood collection vial, a medication vial, an ampule, an injection port or the like, for administering an injection (or withdrawing or collecting from the site bodily fluids, medications, or the like).

Upon completion of the injection delivery, sheath 20 will resiliently return toward the fully extended condition of FIG. 4. The user of the medical instrument to which needle assembly 10 is attached may then exert a distal force on outwardly extending flange 42 of collar 36 to disengage the recesses 106 from barbs 104 so as to free collar 36 from the sheath 20. Collar 36, once freed, will then be propelled distally under forces exerted by coil spring 30, as coil spring 30 expands toward its unbiased condition. After sufficient distal movement, actuator tab 54 of cap 50 will engage frustrum-shaped distal end 24 of sheath 20. This engagement of actuator tab 54, combined with the continuing distal propulsion of collar 36 under the action of the expanding spring 30 and assisted by the biasing action of leaf spring 100 against arm portion 102 will cause cap 50 to rotate about hinge mounts 44. Tip guard 52 then will assume the orthogonal alignment relative to needle cannula 20 as depicted most clearly in FIG. 6.

In addition, it will be understood that barbs 104/recesses 106 may be configured for self-release upon termination of an injection delivery. One way of accomplishing this is to dimension the components of the device so that upon the injection phase, sheath 20 will move further proximally along the needle cannula so as to cause barbs 104 to unseat from recesses 106. Thus, upon termination of the injection phase and withdrawal of the needle cannula, the coil spring 30 can automatically propel cap 50 without the need to apply an external distal force on the flange 42.

A proximally directed force onto cap 50 in the FIG. 6 position will merely urge rigid and substantially impenetrable tip guard 52 into contact with distal tip 16 of needle cannula 12. These proximally directed forces will work against an opening of cap 50 that could re-expose distal tip 16. The biasing action of leaf spring 100 will also assist to retain the cap in a closed position. Intentional re-exposure of needle cannula 12, however, can be readily achieved by merely exerting proximally directed manual forces on actuator flange 42 of collar 36. In response to proximal forces on actuator flange 42, tip guard 52 will engage the distal end 24 of sheath 20 and rotate about hinge mounts 44 to re-expose distal tip 16 of needle cannula 12 for administering additional doses of a drug or for withdrawing additional fluid. After such subsequent use of needle cannula 12, spring 30 will cause the re-shielding of distal tip 16 of needle cannula 12 as explained above.

Figure 7:
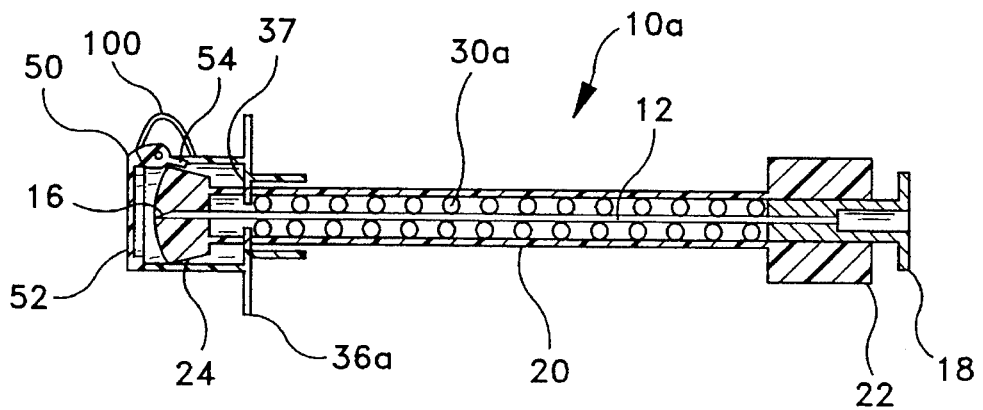
FIG. 7 is a cross-sectional view similar to FIG. 6, but showing the spring disposed between the sheath and the needle cannula.
Figure 8:
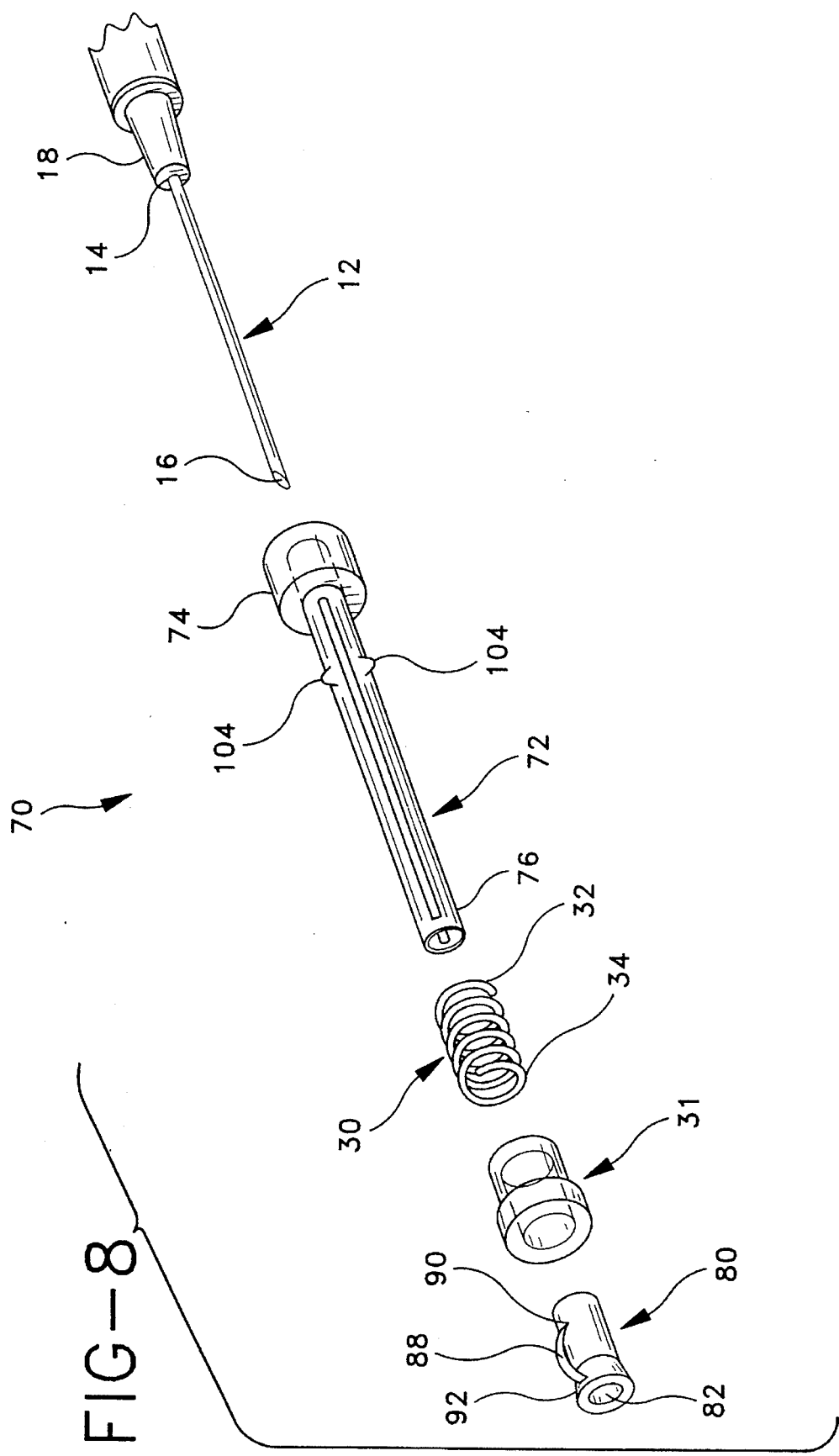
FIG. 8 is an exploded cross-sectional view of an alternate needle assembly in accordance with the subject invention.

As noted above, spring 30 of needle assembly 10 primarily performs a propelling function and not a constricting function. Thus, spring 30 can be located interiorly of sheath 20 as depicted, for example, in FIG. 7, and the propelling function performed from therein. More particularly, a needle assembly 10a has a needle cannula 12 and a collapsible sheath 20 substantially as described above and illustrated in FIGS. 2–6. Collar 36a also is substantially similar to collar 36 described and illustrated above. However, collar 36 includes inwardly directed projections 37 which extend into longitudinally extending slots (not shown) of sheath 20. Coil spring 30a, while functionally similar to spring 30 described above is, however, disposed intermediate needle cannula 12 and sheath 20. A leaf spring 100 may also be provided as earlier described. Needle assembly 10a functions in exactly the manner described above. However, coil spring 30a acts on inwardly projections 37 for propelling collar 36a distally and causing actuator tab 54 of cap 50 to contact frustrum-shaped distal end 24 of sheath 20 to rotate tip guard 52 of cap 50 into orthogonal alignment with distal tip 16 of needle cannula 12.

An alternate needle assembly is illustrated in FIGS. 8–11 and is identified generally by the numeral 70. Needle assembly 70 includes a needle cannula 12 and a coil spring 30 substantially as described and illustrated above. However, spring 30 includes an actuating collar 31 mounted against the distal end 34 of the spring. Needle assembly 70 further includes a sheath 72 structurally and functionally very similar to the sheath 20 described above. Sheath 72 includes a proximal end 74 defining a hub and a distal end 76. The portion of the sheath 72 intermediate the hub and distal end can be formed in a collapsible configuration. Additionally, as before, recesses or other structures 106 may be formed on the collar 31 for engagement with barbs 104 formed on the sheath.

A generally tubular clip guide 80 is attached to distal end 76 of sheath 72. Clip guide 80 includes a generally cylindrical passageway 82 extending therethrough and a pair of transverse slots 84 and 86 extending into passageway 82.

Figure 9:
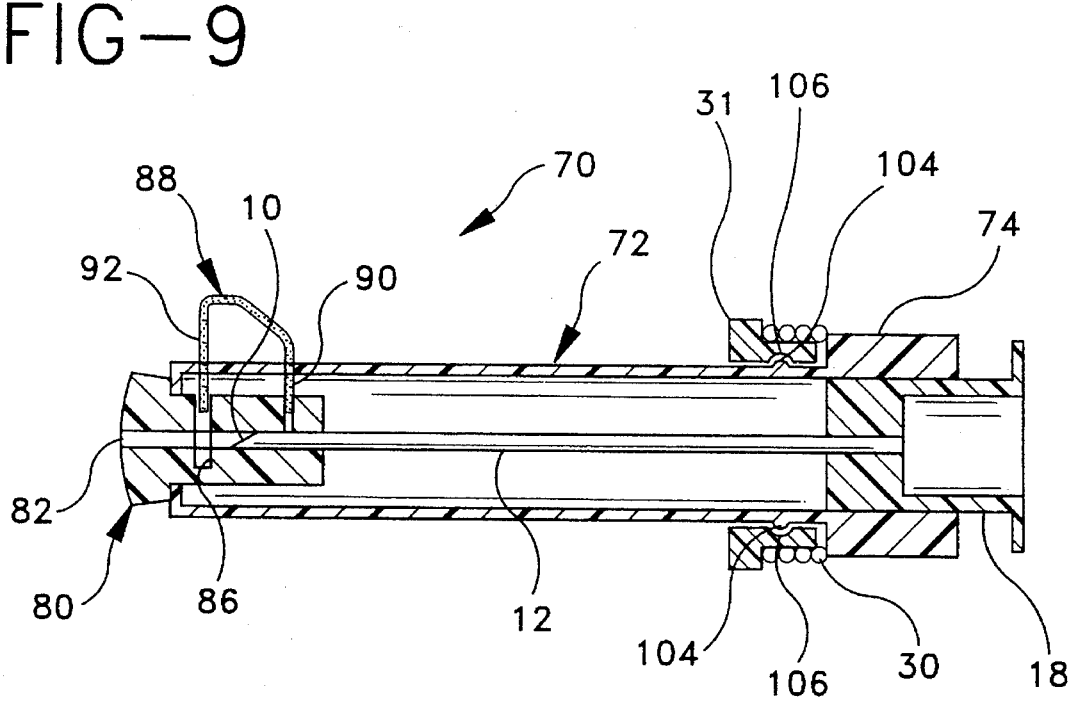
FIG. 9 is a cross-sectional view similar to FIG. 4, but showing the alternate needle assembly of FIG. 8.
Figure 10:
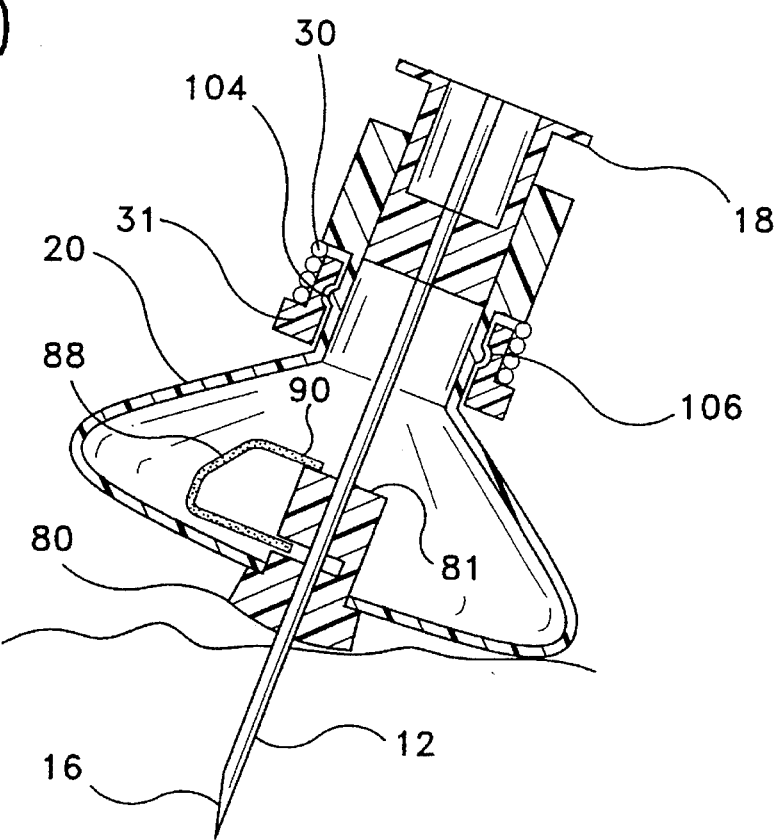
FIG. 10 is a cross-sectional view similar to FIG. 5, but showing the alternate needle assembly of FIGS. 8 and 9.
Figure 11:
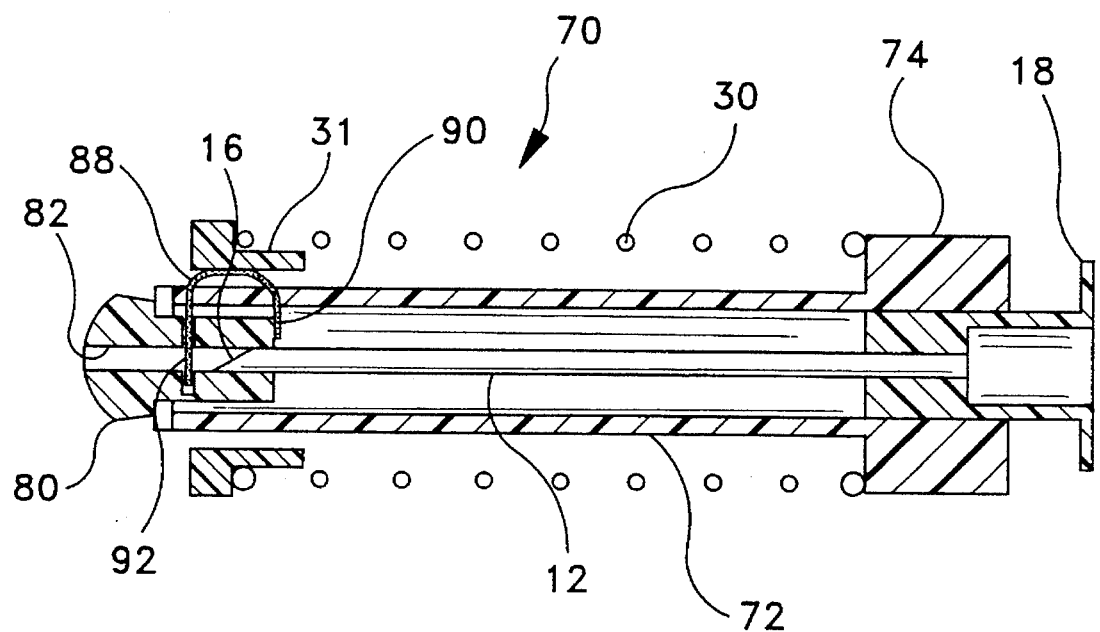
FIG. 11 is a cross-sectional view similar to FIG. 5, but showing the needle assembly of FIGS. 8-10.

A generally U-shaped spring clip 88 is provided with opposed substantially parallel proximal and distal legs 90 and 92 which extend respectively into transverse slots 84 and 86, as shown in FIG. 9. Alternately, as depicted in FIGS. 10 and 11, distal leg 92 may be guided by its transverse slot 86, with the proximal leg 90 of spring clip 88 securely engaged against the proximal end surface 81 of clip guide 80 by the biasing action of the spring. As shown, proximal leg 90 of spring clip 88 may be configured shorter than distal leg 92 so as 70 to upwardly ramp the profile of spring clip 88 as it extends from its proximal end to its distal end. Spring clip 88 can be moved between a blocking position where distal leg 92 extends entirely across passageway 82 and a nonblocking position where neither leg blocks passageway 82. The FIG. 9 position of needle assembly 70 is comparable to the FIG. 4 position of needle assembly 10 described and illustrated above. More particularly, clip guide 80 and sheath 72 extend beyond distal tip 16 of needle cannula 12. However, sheath 72 can be collapsed in a proximal direction, as shown in FIG. 10, by forces exerted by the injection site such such as the skin, a vial or an injection port as distal tip 16 of needle cannula is urged for injection.

Sheath 72 will resiliently return toward its undeflected condition when needle cannula 12 is withdrawn from the patient. As previously described, by disengaging recesses 106 from barbs 104, collar 31 then can be manually released from its engagement adjacent hub 74 of sheath 72 such that spring 30 propels collar 31 distally. As spring 30 approaches its maximum extension, collar 31 will slide over outer portions of U-shaped spring clip 88, assisted by the ramped configuration of the spring clip and will urge U-shaped spring dip 88 inwardly. In this position, distal leg 92 of spring clip 88 will be urged through transverse slot 86 and entirely across passageway 82 to completely cover distal tip 16 of needle cannula 12. In this position, any proximally directed forces on clip guide 80 will merely urge spring clip 88 into engagement with distal tip 16 of needle cannula 12.

The metallic material from which spring clip 88 is formed is substantially impenetrable by needle cannula 12, and hence accidental needle sticks are prevented. Additionally, any minor proximal movement of clip guide 80 relative to needle cannula 12 will generate tighter engagement between collar 31 and outer portions of spring clip 88.

Figure 12:
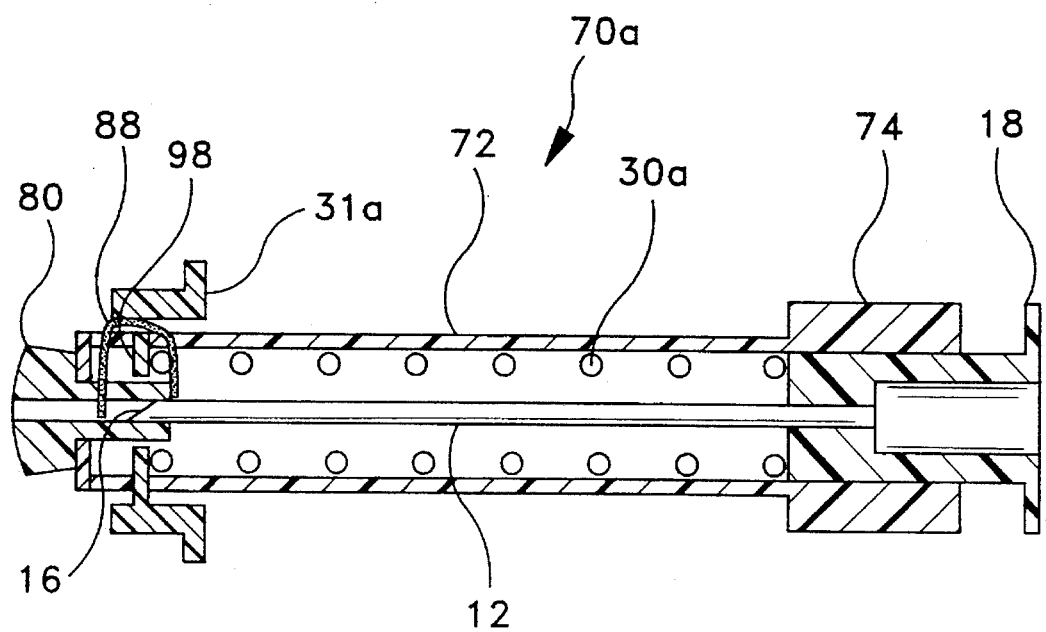
FIG. 12 is a cross-sectional view similar to FIG. 11, but showing an alternate embodiment with the spring intermediate the collapsible sheath and the needle cannula.

As noted above, spring 30 performs a propelling function and not a constricting function relative to sheath 72. As a result, spring 30 need not tightly engage sheath 72, and free propelling movement of spring 30 is ensured without binding against sheath 72. FIG. 12 shows a needle assembly 70a with a needle cannula 12, a sheath 72, a dip guide 80 and a spring dip 88 all as described and illustrated with respect to FIGS. 8–11. A collar 31a on needle assembly 70a differs slightly from collar 31 in that it includes inward projections 98 which extend through slots in sheath 72. A spring 30a is disposed within sheath 72 and is biasingly engaged with projections 98 of collar 31a. After completion of an injection, collar 31a is disengaged and propelled distally. Collar 31a will engage over spring clip 88 to urge spring clip 88 inwardly and over distal tip 16 of needle cannula 12.

Needle cannula 12 can be re-exposed in the embodiments depicted in FIGS. 8–12 substantially as in the previously described embodiments. In particular, proximally directed forces on collar 31 or 31a will urge the collar and the coil spring proximally back toward the FIG. 9 position. This will permit spring clip 88 to disengage outwardly relative to clip guide 80 and needle cannula 12. Then, proximally directed forces on clip guide 80 will cause a collapsing of sheath 72 for the intentional re-exposure of needle cannula 12.

It will be understood and realized by those skilled in the art that further and additional forms of the invention may be devised without departing from the spirit and scope of the appended claims, the invention not being limited to the specific embodiments shown.

What is claimed is:

1. A needle assembly comprising:

a needle cannula having a pointed tip;

a first collapsible member surrounding at least a portion of said needle cannula and being resiliently biased toward an expanded condition in which a portion of said first collapsible member approaches said tip;

a tip guard mounted to said first collapsible member for selective movement toward and away from said needle cannula; and a second collapsible member disposed intermediate said first collapsible member and said needle cannula and surrounding at least a portion of said needle cannula, said second collapsible member being resiliently biased toward and expanded condition in which a portion of said second collapsible member approaches said tip, said second member being configured to activate said tip guard and move said tip guard into covering relationship with said tip when said first and second members are in said respective expanded conditions.

2. The needle assembly of claim 1, wherein said tip guard is pivotally mounted to said first collapsible member.

3. The needle assembly of claim 2, wherein said tip guard includes an actuator tab, and wherein said second collapsible member includes a tapered surface for engaging said actuator tab and moving said tip guard into covering relationship with said tip of said needle cannula when said first and second members are in said respective expanded conditions.

4. The needle assembly of claim 3, further comprising an element in biasing engagement with said tip guard for biasing said tip guard into covering relationship with the tip of the needle cannula.

5. The needle assembly of claim 1, wherein the first collapsible member comprises a coil spring.

6. The needle assembly of claim 5, wherein said second collapsible member comprises a collapsible sheath.

7. The needle assembly of claim 1, wherein portions of said first collapsible member are disposed intermediate said second collapsible member and said needle cannula.

8. The needle assembly of claim 1, wherein said first collapsible member is releasably engageable in a collapsed condition.

9. The needle assembly of claim 8, wherein said second collapsible member comprises one or more projections formed on the exterior surface of said member, and said tip guard comprises one or more elements formed to releasably engage said one or more projections formed on the second collapsible member.

10. The needle assembly of claim 1, wherein said tip guard comprises a metallic spring clip resiliently engaged in said second collapsible member for selective movement toward and away from said needle cannula.

11. The needle assembly of claim 8, wherein said first collapsible member is disposed intermediate said second collapsible member and said needle cannula, said tip guard mounted to said first collapsible member via a projection through said second collapsible member, said tip guard disposed about said second collapsible member.

12. The needle assembly of claim 9, wherein said first collapsible member comprises a coil spring.

13. The needle assembly of claim 12, wherein said second collapsible member comprises a collapsible sheath having portions surrounding said pointed tip of said needle cannula in said expanded condition of said first collapsible member.

14. The needle assembly of claim 1, wherein said first collapsible member is releasably engageable in a collapsed condition.

15. The needle assembly of claim 1, wherein the first collapsible member comprises elastomeric collar.

16. The needle assembly of claim 1, wherein the first collapsible member comprises a resilient bellows.

17. A needle assembly comprising:

a needle cannula having opposed proximal and distal ends;

an elongate sheath at least partially surrounding said needle cannula and having opposed proximal and distal ends, said sheath being collapsible proximally for selectively exposing said distal end of said needle cannula;

a coil spring at least partially surrounding said needle cannula and having opposed proximal and distal ends, said distal end of said spring being releasably compressible towards said proximal end thereof and being disposed proximally of said distal end of said sheath, such that release of said distal end of said spring propels said distal end of said spring toward said distal end of said sheath; and a tip guard pivotally mounted to said spring and being configured such that said propelling of said distal end of said spring toward said distal end of said sheath urges portions of said tip guard into contact with said sheath, and pivots said tip guard over said distal end of said needle cannula.

18. The needle assembly of claim 17, wherein said coil spring includes a collar mounted to said distal end thereof for movement therewith, said tip guard being pivotally mounted to said collar.

19. The needle assembly of claim 17, further comprising an element in biasing engagement with said tip guard for biasing said tip guard over said distal end of the needle cannula.

20. The needle assembly of claim 18, wherein said distal end of said sheath comprises an outwardly tapering surface, said tip guard engaging with said surface as said collar is propelled toward said distal end of said sheath for pivoting said tip guard over said distal end of said needle cannula.

21. The needle assembly of claim 17, wherein said spring is disposed around said sheath.

22. The needle assembly of claim 17, wherein said spring is disposed intermediate said sheath and said needle cannula.

23. The needle assembly of claim 17, wherein said tip guard includes a metallic insert for preventing penetration of said tip guard by said needle cannula.

24. The needle assembly of claim 17, wherein said distal end of said spring is releasably engageable adjacent said proximal end of said sheath.

25. The needle assembly of claim 18, wherein said elongate sheath comprises one or more projections formed on the exterior surface of said sheath, and said collar comprises one or more elements formed to releasably engage said one or more projections formed on the sheath.

26. A needle assembly comprising:
   a needle cannula having opposed proximal and distal ends;
   an elongate sheath surrounding said needle cannula and having opposed proximal and distal ends, said sheath being collapsible proximally for selectively exposing said distal end of said needle cannula;
   a coil spring surrounding said needle cannula and having opposed proximal and distal ends, said distal end of said spring being releasably compressed towards said proximal end thereof and being disposed proximally of said distal end of said sheath, such that release of said distal end of said propels said distal end of said spring toward said distal end of said sheath; and
   a tip guard mounted to the distal end of said sheath, said tip guard comprising a generally u-shaped spring clip mounted for movement toward and away from said needle cannula, said tip guard being configured such that said propelling of said distal end of said spring toward said distal end of said sheath urges said spring clip in covering relationship over said distal end of said needle cannula.

27. The needle assembly of claim 26, wherein said spring surrounds said sheath.

28. The needle assembly of claim 26, wherein said spring is disposed between said needle cannula and said sheath, said spring including a collar mounted to said distal end of said spring and having portions disposed exteriorly of said sheath for engaging portions of said spring clip and urging said spring clip in covering relationship over said distal end of said needle cannula as said distal end of said spring is propelled toward said distal end of said collar.

* * * * *